United States Patent [19]

Georgieva et al.

[11] Patent Number: 4,816,483

[45] Date of Patent: Mar. 28, 1989

[54] COMPOSITION AND METHOD FOR TREATMENT AND METAPHYLAXIS OF URATE AND MIXED URATE LITHIASIS

[75] Inventors: Maria I. Georgieva; Georgi M. Georgiev, both of Sofia, Bulgaria

[73] Assignee: TPO "Pharmachim", Sofia, Bulgaria

[21] Appl. No.: 795,424

[22] Filed: Nov. 6, 1985

Related U.S. Application Data

[63] Continuation-in-part of Ser. No. 580,089, Feb. 14, 1984, abandoned.

[51] Int. Cl.$^4$ .............................................. A61K 31/20
[52] U.S. Cl. .................................................... 514/558
[58] Field of Search ................ 252/DIG. 1, DIG. 14; 514/558

Primary Examiner—Stanley J. Friedman
Attorney, Agent, or Firm—Klein & Vibber

[57] ABSTRACT

A combination and method for treatment and metaphylaxis of urate and mixed urate lithiasis is disclosed. The active component of the invention is a non-ionogenic surfactant of the formula $R\text{-COO}(CH_2CH_2O)_nH$, wherein R is linolic acid, linolenic acid, or oleinic acid, and n is a number from 18 to 40. The active component forms a complex water-soluble compound with uric acis, thereby dissolving urate calculi and eliminating uric acid from the urine. The invention exhibits rapid and reliable therapeutic effect, without side effects, and without reliance on maintenance of urine pH.

2 Claims, 4 Drawing Sheets

FIG. 3

|  | urine (healthy) | our remedy | Soluran | Our remedy and urine | Soluran and urine |
|---|---|---|---|---|---|
| density | 1.010 | 0.997 | 1.004 | 1.006 | 1.017 |
| surface tension | 57,57 N/m | 42.92 N/m⁻ | 73.04 N/m⁻ | 54.05 N/m⁻ | 70.30 N/m⁻ |

COMPOSITION AND METHOD FOR TREATMENT AND METAPHYLAXIS OF URATE AND MIXED URATE LITHIASIS

This application is a continuation-in-part of a Ser. No. 580,089, filed Feb. 14, 1984 now abandoned.

BACKGROUND OF THE INVENITON

This invention relates to a medicinal means for treatment and metaphylaxis of urate, urate-oxalate and urate-phosphate lithiasis. Nephrolithiasis is a very common urological disease characterized by the presence of renal calculi, small hard concretions of urate, oxalate, cysteine, and phosphate deposits which accumulate in the kidney. Nephrolithiasis is most often treated by surgical intervention. Pharmaceutical litholysis, the nonsurgical and medicinal dissolution of calculi, is known, but these methods are generally slow and of limited reliability for wide spread therapeutic use.

Urate and mixed urate lithiasis has been treated in the past with preparations containing various salts, such as sodium and potassium citrates, bicarbonates, and citric acids. Preparation of this type include those known by the trade names Magurlite ®, Solurane ® and another composition, Uralite ®, which contains certain medicinal plant extracts useful for litholysis. All of these compositions rely on the ability of the salts or extracts to maintain a pH of 7 in the urine, thus hampering the crystallization of uric acid in patients prone to renal lithogenesis.

The Magurlite ® preparation is a Hungarian preparation. Its composition is as follows:
Pyridoxine hydrochloride 0.008
Magnesium citrate 0.18
Sodium citrate 0.723
Potassium citrate 0.794
Citric acid 0.27.

It is provided in the form of granules in 2 grs. bag and is applied in cases of urate lithiasis. It acts also in cases of renal calculi containing oxalates. The mechanism of action lies in alkalizing the urine. It is not applied in cases of infected forms of lithiasis and circulation disturbances.

The Solurane ® preparation is a Bulgarian preparation. It has the following composition:
Potassium bicarbonate 35.6
Sodium citrate 30.6
Citric acid sic.. 33.7
Corrigent to 100.

The preparation is applied in cases of urate lithiasis. It is not applied in infected forms and mixed forms of the disease. The mechanism of action lies in alkalizing the urine up to pH-7.

The Uralyte ® preparation is a West German preparation.

Its composition is the following:
Sodium citrate 35.0
Potassium bicarbonate 36.7
Citric acid 33.2
Corrigent to 100.

Its mechanism of action also lies in alkalizing the urine. It is applied in cases of urate lithiasis. The preparation has no application in cases of infected forms of the disease.

All these known preparations' act by dissolving the concrements by means of alkalizing the urine and dissolving the uric acid. The action according to the present invention is different:

(a) reducing the surface urine tension in cases of lithiasis where said tension is higher than in the urine of healthy people;

(b) forming with the uric acid (from the concrements) a water-soluble complex composition without changing the reaction of urine.

The "active ingredient" of the inventive means is not a "basic ingredient" in the sense of one with a basic chemical character. On the contrary, it is provided by a neutral chemical reaction. The active ingredient is a mixture of ⅔ monoester and ⅓ diester of polyetheleneglycol with higher unsaturated fatty acids having a molecular weight of about 1000.

The known preparation suffer from a number of disadvantages. First, it is difficult to accurately maintain the physiological pH at the desired therapeutic level throughout administration of the preparations. The pH may increase beyond 7, allowing phosphate precipitation in the alkaline urine. Thus, the kidney infection may proceed despite administration of the known preparations. Second, the known compositions work very slowly. They require clinical administration over a period of several months before any therapeutic result is evident. Third, the known compounds are toxic, and patients often suffer from side-effects during the long course of treatment. Fourth, the known compounds are not suitable for infectious or mixed urate forms of lithiasis.

SUMMARY OF THE INVENTION

It is, therefore, an object of the present invention to provide a pharmaceutical preparation for the treatment and metaphylaxis of urate and mixed urate lithiasis, by providing rapid and reliable dissolution of urate concretions. Rapid and reliable litholysis is achieved by an active component comprising a non-ionogenic surface active substance, or surfactant. The surfactant of the present invention is of the general formula I:

$$R\text{---}COO(CH_2CH_2O)_nH \qquad (I)$$

where R is an anion of linolic, linolenic or oleinic acid and n is a number from 18 to 40.

Besides the active ingredient (i.e. to the non-ionogenous surface-active substance), the inventive preparations contain 10% corrigents and 0.1% conservatives. The latter do not alter the action of the active ingredient, this having been proven in vitro and in vivo by means of their inclusion concurrently, as well as separately.

The basic component according to the invention is a mixture of ⅔ mono-ester and ⅓ diester of polyethleneglycol-1000 and hgher fatty acids corresponding to [R] of the acids recited in formula I, supra.

According to the present invention, complex water-soluble compounds are formed with uric acid to both dissolve the urate concretions and eliminate uric acid through the urine.

More specifically, new chemical bonds are created between the uric acid, (more precisely, the nitric atom of the imidazole nucleus of its keto form), and the oxygen atom of the polyethyleneglycolic chain of the non-ionogenous surface-active substance (i.e. the basic ingredient of the inventive means). This has been proven by means of UV- and NMR-Spectra.

The medicinal means according to the invention for treatment and metaphyloxis of urate and urate-mixed forms of the kidney disease differs in principle from all known medicinal means. The preparations proposed by different firms for treating urate lithiase are based upon the active components (mostly salts), which change the value of the pH of urine from 5-5.5 to about 7. This aims at preventing the uric acid from precipitating and crystallizing, i.e. at hampering the growth of renal concrements and dissolving them.

The medicinal means according to the invention forms a water-soluble complex between the uric acid and the active means component (in this case—a non-ionogenic surface-active substance), said complex eliminating the uric acid from the concrements and hampering the precipitation of newly formed uric acid. This action is realized without changing the pH of the urine of the patient, and the effect is quicker and more efficient.

The medicinal means according to the invention has undergone experimentation in vitro on test animals with a complete toxicological and pharmacological characterization carried out. The clinical tests also show an effect in 80% of the cases of urate lithiase with no side effects. The sick take the medicine quite easily, and their working capacity is reestablished very soon.

The means of the invention are comparatively simple technologically. It contains: a non-ionogenic surface-active substance MGI57 (ester of polyethyleneglycol-1000 and higher fatty acids containing 16-40 carbon atoms). This ester contains a remainder of the higher fatty acid which is bound, through an ester bond with the carboxylic group, with 22 remainders of the polyethyleneglycol: $(-CH_2-CH_2-O-)_{22}$. The non-ionogenic surface-active substance is provided as a concentration of 2.5% in distilled water in the preparation. The content of Sorbitol is 10%, and that of Nipag and Nipazol is 0.1%. The storage durability of the preparation is one year. The surface-active substance MGI57 is dissolved at a temperature of 38° C., with constant stirring, in distilled water. Sorbitol, Nipagin and Nipazol in the above quantities are added consecutively and constantly stirred. The preparation, prepared in this manner in the form of syrup, is filtrated and kept in dark glass containers of 300 ml.

A method exists for standardization and control over the proposed medicinal means. A method exists for quantity and quality assurance check, based upon UV-spectral analysis or spectro-photometry at 620 nm.

The complex-forming process between the keto-form of the uric acid (in this form it builds-up the urate concrements) and the hydrated molecules of the non-ionogenic surface-active substance MGI57 is proven by means of UV-spectral and IR-spectral methods, as well as ion-exchange chromatography. The complex-formation scheme is represented as follows:

SCHEME OF COMPLEX FORMATION

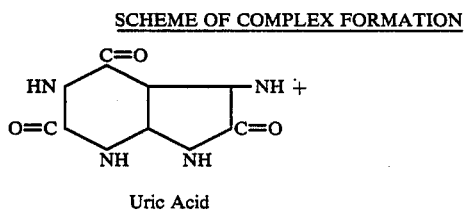

Uric Acid

-continued
SCHEME OF COMPLEX FORMATION

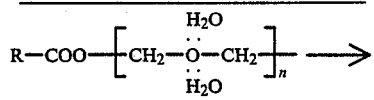

Surface-Active Compound

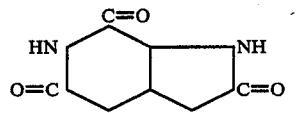

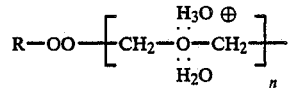

Complex Compound

R ———⟶ Acid (C-18-40)

n ———⟶ 22-40

The present invention achieves a number of advantages over litholysis preparations already known. First, the new preparation acts quickly. Beneficial results are usually evident within a month. Second, the preparation exhibits no secondary effects. Third, it is useful for infectious and mixed-urate (urate-oxalate and urate-phosphate) forms of lithiasis. Fourth, it does not alter the pH of urine and does not rely on acid-base equilibrium to prevent lithogenesis. There is no inherent danger of precipitation, as in the methods and preparations heretofore known.

BRIEF DESCRIPTION OF THE DRAWINGS

FIG. 3 provides surface tension data.

PREFERRED EMBODIMENTS

It has been proven by UV-spectra that the means according to the invention is more effective than the Solurane ® preparation.

Figure 1:
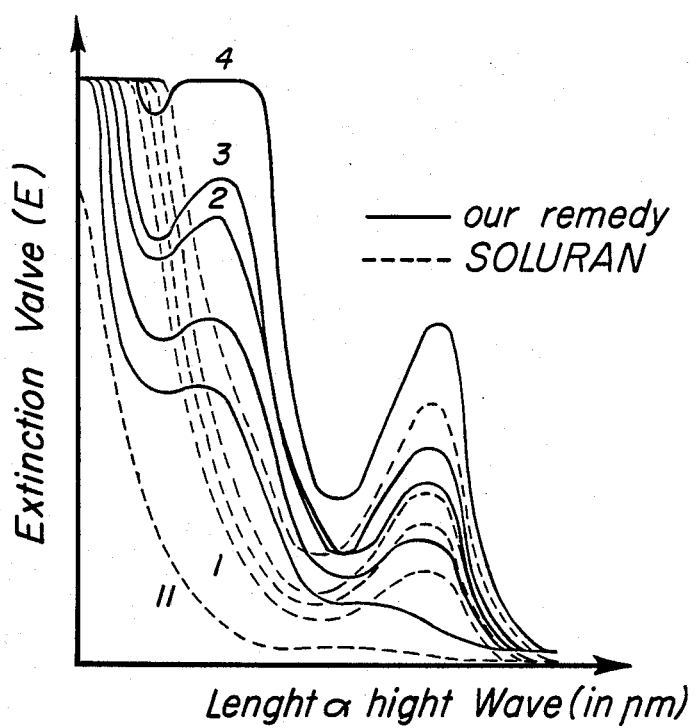
FIG. 1 shows UV-spectra of dissolved uric acid.

Tests were carried out in vitro with solutions having a concentration of 0.1%, rendering an account of the dissolved uric acid in the concrements according to its typical peak at 286 nm (FIG. 1).

Figure 2:
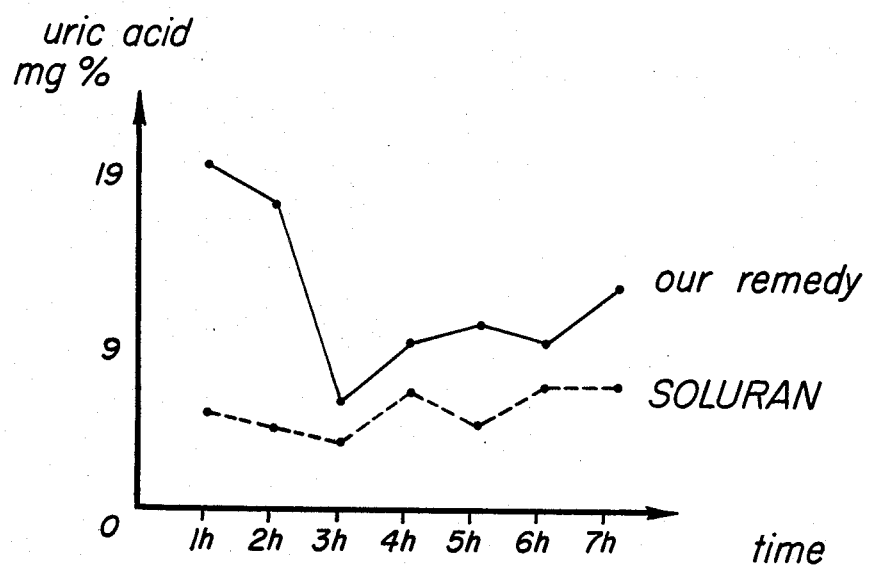
FIG. 2 shows results of tests carried out in systems resembling the function of kidneys, at a temperature of 37° C.

The higher efficiency of the inventive preparation is obvious from FIG. 2, which contains results of tests carried out in systems which resemble the function of kidneys at a temperature of 37° C.

Figure 4:
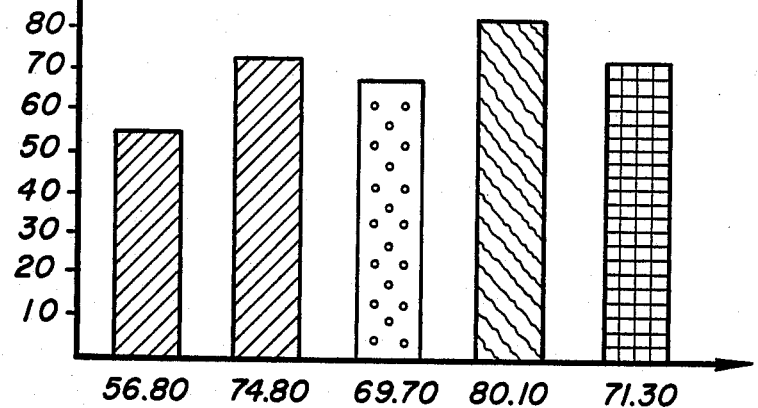
FIG. 4 provides uric acid surface tension data, in the case of people suffering from nephrolithiasis.

It is known that the uric acid surface tension is increased in the case of people suffering from nephrolithiasis. This is obvious from our research as reflected in FIG. 4. The inventive means reduce this tension, thus disturbing the stability of the concrements. The preparation Solurane ® lacks this ability (FIG. 3).

The analysis of ester is carried out by the method of Malkemus-Swan (Y.Amer.Oil. Chem., 34, 1975,342), UV-spectra peak at 272 nm and YR-spectra: peaks at 1740 $cm^{-1}$ (ester group). We trace thereby also the elimination of the preparation with the urine of healthy persons. In the case of sick persons, replacement and deformation of said peaks is observed (combination with the peak at 286 nm of the uric acid).

Clinical researches were carried out in three hospitals for nephrology and urology, indicated by the Allowance and Use of Medical Preparations in Bulgaria Committee. The research is represented in reports which show the preparation efficiency. The conclusion thereof states:

"The new preparation for treatment and metaphylaxis of urate and mixed urate lithiasis has a high uricolytic effect. It is proved in the case of 70-80% of the sick persons treated therewith. It has no side and allergic effects. It is applied successfully in cases of infected nephrolithiasis forms ... ".

Examples and clinical data relating to the present invention are set forth below. It will be appreciated by those skilled in the art that these exemplary embodiments are presented solely for the purpose of exposition and are not to be construed as limiting.

The preparation is applied per os three to four times daily in single doses of 0.375 g each, generally one hour before meals, with an average period of treatment ranging from 20 days to 3 months, depending upon the concrement size. The active compound can be administered in syrup, tablet, or gelatin-capsule form using known medicinal carriers.

The effect of the present invention on urate calculi in vitro was demonstrated by experiments conducted at 37° C. under static conditions. Samples of urate, urate-oxalate, and uratephosphate concretions were analyzed to determined their mass and uric acid content. The samples were placed in a 2.5% aqueous solution of the active compound. Reduction in mass of the concretions and change in uric acid content were monitored. The average mass reduction of the samples after exposure to the active compound for 48 hours was approximately 20%.

Similar tests conducted with samples in a urine medium resulted in an average mass reduction of 23% in 48 hours.

In order to test the effectiveness of the invention under dynamic conditions, experiments simulating the human elimination system were conducted. These revealed an average mass reduction of 44.7%.

Comparative tests between Solurane®, a known litholysis preparation, and the present invention were performed under static and dynamic conditions. Under static conditions, Solurane® produces average mass reduction of urate calculi of 7.1%. The compounds of the present invention produce an average mass reduction of 19.6%. Under dynamic condition, Solurane® produces an average mass reduction of 21.9%, while the present invention achieves 44.7%.

Ultra-violet spectra of the active compounds were obtained both before and after reaction with the urate concretions. The compounds of the invention possess a characteristic UV spectrum with peaks at 262 nm, 272 nm, and 284 nm. Following the reaction with the urate calculi, uric acid from the reaction mixture exhibits a spectrum peak at 286 nm. The characteristic spectrum of uric acid in distilled water exhibits a peak at 290 nm. Thus, a shift in the characteristic spectrum has occurred. The shorter wavelength indicates that uric acid is present in solution in the form of a complex compound, not as a free acid. The mechanism of the present invention therefore involves the formation of a complex compound whereby urate solids are dissolved and uric acid is eliminated. Both the mechanism of the reaction and the compounds formed are heretofore unknown in the art.

Toxicity was determined by tests on laboratory animals under acute and chronic experimental conditions. The average lethal dose was found to be $LD_{50}=3680$ mg/kg for per os administration of the drug. No irritating action on mucous membranes, hypodermic tissue, or muscular tissue has been observed. There are no changes in blood pressure, erythrocyte levels, or enzyme levels. No alteration of the internal organs is indicated.

Experiments were performed to establish elimination of the present compounds from the human kidney. A control group of healthy persons not suffering from nephrolithiasis were tested for the following urine parameters: pH, surface tension, and uric acid content. The control group was given a single 0.375 dose of the drug in a spoonful of syrup containing 2.5% of the active component. The control group was found to eliminate the compound within 20 minutes to one hour after ingestion, as shown by ultra-violet analysis of the urine. The urine also showed an average reduction in surface tension of approximately 6.5 dyn/cm. There was no change in urine pH. There was also no change in uric acid content, except that the uric acid was now bound in the form of a complex compound.

An experimental group of patients suffering from urate or mixed urate lithiasis was tested. Each patient was given a spoonful of syrup containing the active compound three times per day, one hour before eating. The patients were examined by urine and blood analysis, x-ray photography, and echography. Litholysis of the urate concretions was found to occur after a period of 20 days to 2 months, depending on concretion size. Relief from symptomatic discomfort was generally evident within the first week of treatment.

We claim:

1. A method for treatment and metaphylaxis of urate and mixed urate lithiasis comprising
   per os adminstration of an effective amount of a composition containing a known inactive pharmaceutical excipient and an active non-ionogenic surfactant compound of the formula R—COO(CH$_2$CH$_2$O)$_n$H, wherein R is an anion of linolic acid, linolenic acid or oleinic acid and n is a number from 18 to 40 to patients suffering from urate an mixed-urate and mixed-urate lithiasis.

2. A method, according to claim 1, for treatment and metaphylaxis of urate and mixed urate lithiasis comprising
   per os adminstration of said composition in single doses of 0.375 g each, three to four times per day;
   subsequent internal exposure of the concretions to said surfactant compound in a urine medium;
   formation of a molecular complex between the surfactant compound and said superficial urate of the concretions;
   release of said urate complex from said concretions into the urine, with a simultaneous decrease in the mass of the concretions; and
   elimination of the urine from the kidneys.

* * * * *